US007179966B2

(12) United States Patent
Secrist et al.

(10) Patent No.: US 7,179,966 B2
(45) Date of Patent: *Feb. 20, 2007

(54) SOYBEAN CULTIVAR 11939-31

(75) Inventors: Ronald E. Secrist, Ames, IA (US); William M. Campbell, Beloit, WI (US); Robert E. Moore, Gibson City, IL (US); Hunt B. Wiley, West Lafayette, IN (US)

(73) Assignee: Dairyland Seed Co., Inc., West Bend, WI (US)

( * ) Notice: Subject to any disclaimer, the term of this patent is extended or adjusted under 35 U.S.C. 154(b) by 287 days.

This patent is subject to a terminal disclaimer.

(21) Appl. No.: 10/827,768

(22) Filed: Apr. 20, 2004

(65) Prior Publication Data

US 2004/0205865 A1  Oct. 14, 2004

Related U.S. Application Data

(63) Continuation-in-part of application No. 10/108,326, filed on Mar. 28, 2002, now Pat. No. 6,734,346.

(60) Provisional application No. 60/280,409, filed on Mar. 30, 2001.

(51) Int. Cl.
- *A01H 5/00* (2006.01)
- *A01H 5/10* (2006.01)
- *A01H 1/00* (2006.01)
- *C12N 5/04* (2006.01)

(52) U.S. Cl. .................. 800/312; 800/260; 435/415
(58) Field of Classification Search .................... None
See application file for complete search history.

(56) References Cited

U.S. PATENT DOCUMENTS

| | | |
|---|---|---|
| 5,986,179 A | 11/1999 | Rhodes |
| 6,005,170 A | 12/1999 | Lussenden |
| 6,143,954 A | 11/2000 | Hicks, Jr. |
| 6,162,972 A | 12/2000 | Matson |
| 6,459,020 B1 | 10/2002 | Nickell |
| 6,870,079 B2 | 3/2005 | Eby et al. |
| 2004/0199996 A1 | 10/2004 | Secrist et al. |

*Primary Examiner*—Anne Kubelik
(74) *Attorney, Agent, or Firm*—Billie Jean Smith; Jill A. Fahrlander; Michael Best & Friedrich LLP

(57) ABSTRACT

Disclosed is the seed of a novel soybean cultivar, designated 11939-31, a sample of which is deposited under ATCC Accession No. PTA-7403. Also disclosed are plants, or parts thereof, grown from the seed of the cultivar, plants having the morphological and physiological characteristics of the 11939-31 cultivar, and methods of using the plant or parts thereof in a soybean breeding program.

16 Claims, No Drawings

SOYBEAN CULTIVAR 11939-31

CROSS REFERENCE TO RELATED APPLICATIONS

This application is a continuation-in-part application of U.S. Ser. No. 10/108,326, filed Mar. 28, 2002 now U.S. Pat. No. 6,734,346, which claims priority to U.S. Provisional Patent Application Ser. No. 60/280,409, filed Mar. 30, 2001, each of which is incorporated by reference herein.

STATEMENT REGARDING FEDERALLY SPONSORED RESEARCH OR DEVELOPMENT

Not applicable.

BACKGROUND OF THE INVENTION

Soybeans are a major grain crop valued for the high levels of oil and protein found in soybean seed. Soybean breeding has resulted in significant improvements in yield potential, stability of yield, adaptation of the species to mechanical harvest, and yield protection through improved disease resistance.

Due to the nature of plant science agriculture, broadly defined as a manipulation of available plant resources to meet the needs of the growing human population, the environment in which plants are grown for agricultural production continuously offers new obstacles to agricultural production. Each new cultivar or variety released to agricultural production is selected for the purpose of increasing yield resulting from increased disease resistance to prevalent diseases, or from direct or indirect improvement in yield potential or efficiency of production. Development of stable, high yielding cultivars with superior characteristics is an ongoing goal of soybean breeders.

There is a need in the art for a novel soybean cultivar and soybean seed.

SUMMARY OF THE INVENTION

In one aspect, the present invention provides a soybean seed designated 11939-31, wherein a sample of said seed has been deposited under ATCC Accession No. PTA-7403.

In another aspect, the present invention provides a soybean plant, or a part thereof, produced by growing seed designated 11939-31, or a soybean plant having the characteristics of a plant produced by growing seed designated 11939-31, or pollen or an ovule of a soybean plant according to the present invention.

The present invention provides a tissue culture of regenerable cells from a plant, or parts thereof, produced by growing seed designated 11939-31, and a soybean plant regenerated from the tissue culture.

The present invention also provides a method for developing a soybean plant in a soybean breeding program using plant breeding techniques, comprising using a soybean plant, or part thereof, produced by growing seed designated 11939-31 as a source of breeding material.

DEFINITIONS

In the claims, descriptions and tables that follow, numerous terms are used and are defined as follows:

Flower color: Modern soybeans are characterized by two major flower colors, purple or white. Some cultivars are heterogeneous for flower color whereby some plants have purple flowers and some have white.

Leaflet shape: The leaflet may be broad or narrow and may be ovate or oval in shape.

Plant habit refers to stem termination in soybeans and the resultant differences in flower production. Indeterminate varieties continue to grow during the reproductive phase, producing new branches and nodes after flowering is well underway. Determinate varieties tend to delay the onset of flowering somewhat, and limit new node and branch development after flowering has been initiated.

Pubescence relates to the plant trichomes or hairs found on the stems, leaves and pods of soybeans.

Pubescence color in modern soybeans may be tawny, gray or light tawny.

Pod color refers to the color of the mature pod wall, as distinct from the color of the pubescence, and in modern soybeans, may be brown or tan.

Hilum refers to the point of attachment of soybean seed to maternal tissue.

Hilum color in modern soybeans may be black, brown, yellow, gray, buff, or imperfect black.

Soybean emergence scores rate the ability of the seedlings to emerge from the soil. A visual score of 1 to 5, taken 10–15 days after planting, is used whereby a score of 1 indicates an excellent emergence vigor and early growth, an intermediate score of 2.5 indicates average ratings, and a 5 score indicates a very poor emergence vigor and early growth.

Plant height is measured from the top of soil to top node of the plant in any convenient unit of length (i.e., inches, centimeters). For the data presented herein, plant height was measured just prior to harvest and is expressed in inches.

Lodging resistance relates to the stature of the plant relative to the ground. Lodging resistance is rated on a scale of 1 to 5. A score of 1 is given to an erect plant. A score of 2.5 is given to a plant that is leaning at a 45-degree angle relative to the ground. A score of 5 indicates a plant lying on the ground.

Maturity date is the date when 95% of pods have turned color from green color to their mature brown or tan color. The maturity date is counted in days and is calculated from January 1.

Maturity group refers to an industry division of groups of varieties based on the zones in which the varieties are adapted. Soybeans mature differentially in response to day-length and thus to latitude where grown. In the soybean production areas of the United States, for example, the northernmost production region of northern Minnesota is planted to soybeans that mature under very long day-lengths during early summer. In the southernmost production regions of the Southeast, soybeans that mature from the influence of short day-length during early summer are grown. Those adapted to northern day-lengths are classified as early-maturing, those adapted to the southern regions are classified as late-maturing. Maturity groups include very long day length varieties (000, 00, 0) and extend to very short day length varieties (VII, VII, IX, X). For example, maturity group I soybean cultivars are typically grown in southern Minnesota, whereas maturity group IV soybean cultivars are typically group in southern Illinois.

Relative maturity: Within maturity groups, a more precise maturity assignment is given that subdivides each maturity group into tenths. For example, a relative maturity of 3.3 is assigned to a late early maturity group III soybean cultivar.

Shattering refers to pod dehiscence prior to harvest resulting in a loss of mechanically harvestable seed. Pod dehiscence involves seeds falling from the pods to the soil. This is visually scored with a 1 to 5 scale comparing all genotypes within a given test. A score of 1 means pods have not opened and no seeds have fallen out. A score of 2.5 indicates approximately 50% of the pods have opened, with seeds falling to the ground and a score of 5 indicates 100% of the pods are opened.

Yield refers to the yield of seed harvested from a soybean crop. Yield data presented herein is expressed as bushels of seed/acre and is the actual yield of the grain at harvest.

*Phytophthora* tolerance to Phytophthora root rot, caused by the fungus, *Phytophthora megasperma* var. *sojae*, is rated on a visual scale of 1 to 5, with a score of 1 being the highest tolerance ranging down to a score of 5 which indicates the plants have no tolerance to Phytophthora. The visual score is based on the amount of disease-induced stunting of above-ground growth and is taken during the period 3–5 weeks prior to harvest.

Brown Stem Rot (BSR) resistance is visually scored from 1 to 5 based on interveinal leaf chlorosis (yellowing) and necrosis due to brown stem rot, which is caused by the fungus, *Phialophora gregata*. A score of 1 indicates no symptoms. Visual scores range to a score of 5 that indicates severe symptoms of interveinal leaf chlorosis and necrosis. Plants receiving scores of 1.0–1.6 are classified as resistant; plants receiving scores of 1.7–2.0 are classified as moderately resistant.

Sclerotinia Stem Rot (SSR) is a soil-borne fungal disease that causes above-ground disease in soybeans. Plants are infected via discharged ascospores that successfully germinate and infect through soybean structures such as flower petals. Colonization of stem tissue ultimately results in loss of yield potential. Cultivars are rated using prevalence and severity scores and converted into an estimated percent yield loss that can be used for comparison to known resistant or susceptible cultivar standards.

Soybean Cyst Nematode (SCN) resistance is based on a comparison of reproduction rates to a known susceptible cultivar as described by Schmitt et al. (Crop Sci. 32:275-277, 1992), which is incorporated by reference herein. A cultivar with a 0–10% percent reproductive rate compared to a known susceptible cultivar is classified as resistant (R); a cultivar with an 11–30% reproductive rate compared to a known susceptible cultivar is classified as moderately resistant (MR); a cultivar with an 31–59% reproductive rate compared to a known susceptible cultivar is classified as moderately susceptible (MS).

Iron-Deficiency Chlorosis (IDC) results when soybeans lack adequate iron. A visual score taken 25–30 days after planting is used to rate iron-deficiency chlorosis. A score of 1 indicates no stunting of the plants or chlorosis of the leaves, and a score of 5 indicates the plants are dead or dying as a result of iron-deficiency chlorosis. A score of 2.5 means plants have intermediate health with some leaf chlorosis.

DETAILED DESCRIPTION OF THE INVENTION

This invention relates to a soybean cultivar designated 11939-31 which was developed by single plant selection from another soybean cultivar, 11939, which was disclosed and claimed in U.S. Ser. No. 10/108,326. Soybean cultivar 11939-31 differs from its "mother" cultivar, 11939, in more than one important characteristic, as described below.

A single plant selection from soybean cultivar 11939 (developed as described in detail in U.S. Ser. No. 10/108, 326) was made in a winter nursery in South America and grown in a progeny row at Gilbert, Iowa in plot 9PR9479-07 in 1999. Seed gathered from this progeny row was used for agronomic and yield trial evaluations in subsequent seasons, and named 11939-31 on Aug. 2, 2000. This new soybean cultivar was characterized for important morphological, agronomic and performance qualities in evaluation trials, greenhouse studies, and disease nurseries. Soybean cultivar 11939-31 has uniformity and stability of its morphological and other characteristics. The variety description information (Table I) provides a summary of characteristics of soybean cultivar 11939-31 plant characteristics. As used herein, "a soybean plant having the physiological and morphological characteristics of soybean cultivar 11939-31" is a plant having the characteristics set forth in Table 1.

Soybean cultivar 11939-31 differs from cultivar 11939 in that 11939-31 breeds true for pure white flower color, and for its *Phytophthora* Root Rot resistance gene, $Rps_1^k$. In addition, soybean cultivar 11939-31 has pure breeding tolerance to STS® herbicide, whereas 11939 does not. The soybean cultivar 11939-31 does not differ significantly from 11939 in important agronomic characteristics such as lodging resistance and plant height (Table 2). In Table 3, the yield and maturity date of soybean cultivars 11939-31 and 11939 are compared. As can be seen in Table 3, the soybean cultivar 11939-31 was found to mature two days earlier than soybean cultivar 11939 in four years of replicated, comparative studies. Therefore, 11939-31 is characterized as a maturity group I soybean cultivar with a relative maturity of 1.9, whereas 11939 is a maturity group II soybean cultivar with a relative maturity of 2.1 (Table 1).

TABLE 1

VARIETY DESCRIPTION INFORMATION FOR 11939-31

Seed coat color: Yellow
Hilum color: Black
Leaflet size: Medium
Leaflet color: Medium-green
Leaflet shape: Ovate
Flower Color: White
Plant habit: Indeterminate
Pubescence color: Light tawny
Pod color: Brown
Maturity group: I
Relative maturity: 1.9
Phytophthora Root Rot resistance: plants have one genotype: $Rps_1^k\ Rps_1^k$
Brown Stem Rot (*Phialophora gregata*): Resistant
Soybean Cyst Nematode Disease: Moderately susceptible
Iron Deficiency Chlorosis Tolerance: 2.6
ROUNDUP ® Herbicide: Resistant
STS ® Herbicide: Tolerant

TABLE 2

Comparison of agronomic properties of soybean cultivars 11939-31 and 11939.

| Years | Cultivar | Lod | PRR Tol | SSR-% | IDC | HT |
|---|---|---|---|---|---|---|
| 4 | 11939-31 | 1.5 | 2.2 | 13 | 3.3 | 31 |
|   | 11939 | 1.5 | 2.5 | 16 | 3.4 | 31 |

TABLE 3

Summary of yield and maturity data of soybean cultivar 11939-31 versus 11939.

| Years | Cultivar | Reps | Yield | Mat Days |
|---|---|---|---|---|
| 4 | 11939-31 | 668 | 50.4 ns | 261 |
|   | 11939 |  | 51.6 | 263 |

The present invention contemplates using the 11939-31 soybean plant, or part thereof, or a soybean plant having the physiological and morphological characteristics of the 11939-31 soybean plant, as a source of breeding material for developing a soybean plant in a soybean breeding program using plant breeding techniques. Plant breeding techniques useful in the developing soybean plants include, but are not limited to, single seed descent, modified single seed descent, recurrent selection, reselection, mass selection, bulk selection, backcrossing, pedigree breeding, mutation breeding, restriction fragment length polymorphism enhanced selection, genetic marker enhanced selection, and transformation. Plant breeding techniques are known to the art and have been described in the literature. For example, see U.S. Pat. No. 6,143,954, which, along with the references cited therein, is incorporated by reference herein.

As used herein, the term "plant" includes plant cells, plant protoplasts, plant cell tissue cultures from which soybean plants can be regenerated, plant calli, plant clumps, and plant cells that are intact in plants or parts thereof. "Plant part" includes, but is not limited to, embryos, pollen, ovules, seeds, flowers, pods, leaves, roots, root tips, anthers, and the like.

One may obtain soybean plants according to the present invention by directly by growing the seed of 11939-31 or by any other means. A soybean plant having all of the physiological and morphological characteristics of 11939-31 can be obtained by any suitable means, including, but not limited to, regenerating plants or plant parts from tissue culture or cuttings. The scope of the present invention is not limited by the method by which the plant is obtained.

DEPOSIT INFORMATION

Seed from soybean cultivar 11939-31, disclosed above and recited in the appended claims, was deposited with the American Type Culture Collection (ATCC), 10801 University Boulevard, Manassas, Va. 20110 on Feb. 23, 2006.

The present invention is not limited to the exemplified embodiments, but is intended to encompass all such modifications and variations as come within the scope of the following claims.

The invention claimed is:

1. A soybean seed designated 11939-31, wherein a sample of said seed has been deposited under ATCC Accession No. PTA-7403.

2. A plant, or a part thereof, produced by growing the seed of claim 1.

3. Pollen of the plant of claim 2.

4. An ovule of the plant of claim 2.

5. A soybean plant, or a part thereof, having all the physiological and morphological characteristics of the plant of claim 2.

6. A tissue culture of regenerable cells from the plant, or part thereof, of claim 2.

7. The tissue culture of regenerable cells of claim 6, wherein the regenerable cells are derived from a plant part selected from the group consisting of leaf, pollen, ovule, cotyledon, hypocotyl, embryo, root, pod, flower, shoot and stalk.

8. The tissue culture of claim 6, wherein the culture is a callus culture.

9. A protoplast produced from the tissue culture of claim 6.

10. A soybean plant regenerated from the tissue culture of claim 6, wherein the plant has all of the physiological and morphological characteristics of a plant produced by growing seed designated 11939-31 and deposited under ATCC Accession No. PTA-7403.

11. A tissue culture of regenerable cells from the plant, or part thereof, of claim 5.

12. The tissue culture of claim 11, wherein the regenerable cells are derived from a plant part selected from the group consisting of leaf, pollen, ovule, cotyledon, hypocotyl, embryo, root, pod, flower, shoot and stalk.

13. A protoplast produced from the tissue culture of claim 11.

14. The tissue culture of claim 11, wherein the culture is a callus culture.

15. A soybean plant regenerated from the tissue culture of claim 11, wherein the plant has all of the physiological and morphological characteristics of a plant produced by growing seed designated 11939-31 and deposited under ATCC Accession No. PTA-7403.

16. A method for producing a soybean cultivar 11939-31-derived soybean plant, the method comprising:
    (a) crossing the soybean plant of claim 2 with a second soybean plant to yield progeny soybean seed; and
    (b) growing said progeny soybean seed to yield a soybean cultivar 11939-31-derived soybean plant.

* * * * *